United States Patent [19]

Kruse et al.

[11] Patent Number: 4,912,226
[45] Date of Patent: Mar. 27, 1990

[54] INTERMEDIATE TO DOPAMINE-β-HYDROXYLASE INHIBITORS

[75] Inventors: Lawrence I. Kruse, Tewin, England; Stephen T. Ross, Berwyn; Eliot H. Ohlstein, Plymouth Valley, both of Pa.

[73] Assignee: SmithKline Beckman Corporation, Philadelphia, Pa.

[21] Appl. No.: 408,029

[22] Filed: Sep. 15, 1989

Related U.S. Application Data

[62] Division of Ser. No. 139,217, Dec. 29, 1987, Pat. No. 4,882,348.

[51] Int. Cl.$^4$ .......................................... C07D 403/12
[52] U.S. Cl. .................................................. 548/336
[58] Field of Search ........................................ 548/336

[56] References Cited

U.S. PATENT DOCUMENTS 3,941,803  3/1976  Gall ..................................... 548/336
4,554,357 11/1985  Verbicky et al. ............... 548/336 X Primary Examiner—Richard A. Schwartz
Attorney, Agent, or Firm—Mary E. McCarthy; Stuart R. Suter; Alan D. Lourie

[57] ABSTRACT

Potent dopamine-β-hydroxylase inhibitors having the Formula

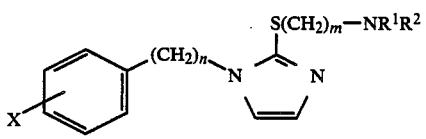

that are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

1 Claim, No Drawings

INTERMEDIATE TO DOPAMINE-β-HYDROXYLASE INHIBITORS

This is a division of Ser. No. 139,217, filed 12/29/87, now U.S. Pat. No. 4,882,348.

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409-432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179-192, and Goldstein, *Pharmacol. Rev.* 18(1), 77 (196), review DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al, *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci.* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non specific interaction of the alkyl substituent with the enzyme. Benzyloxyamine and benzylhydrazine are phenethylalamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172-177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "New Antihypertensive Drugs", Spectrum Publications, 1976, pg. 409-432, to be a DBH inhibitor that has antihypertensive activity.

In European Patent Application No. 125,033 published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

Non specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non specifically to produce the observed side effects.

Iverson, *Acta Chem. Scand.* 21, 279 (1967) reports compounds having the formula:

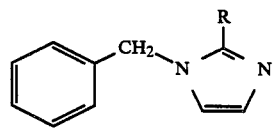

wherein R can be —$CO_2H$ or —$CH_2NHC_6H_5$, but does not report pharmaceutical uses for the compounds.

In neoprene rubber vulcanization mixtures, 1,3-dihydro-4-phenyl-2H-imidazole-2thione has been used as a vulcanization accelerator. *Elastomers* 92:165013u (1980).

SUMMARY OF THE INVENTION

The present invention resides in the discovery that DBH is inhibited by substituted 2-aminoalkylthio-1-aralkylimidazoles, and the mono or di $C_{1-4}$alkylamino derivatives thereof. These compounds are potent long acting DBH inhibitors.

The presently preferred compound of the invention and the compound included in the pharmaceutical compositions and used in the methods of the invention is 2-(2-aminoethylthio)-1-(3,5-difluorobenzyl)imidazole.

In a further aspect of the invention there are provided novel intermediates useful in preparing substituted 2-aminoalkylthio-1-aralkylimidazoles.

The invention also is a method of inhibiting DBH activity in mammals, including humans, which comprises administering internally to a subject an effective amount of a substituted 2-aminoalkylthio 1-aralkylimidazole or a mono- or di-$C_{1-4}$alkylamino derivative thereof.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

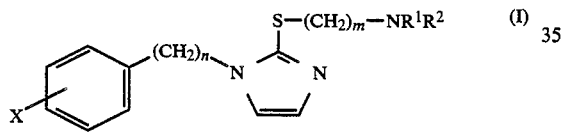

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1-5, or any accessible combination thereof of up to 5 substituents;

n is 0-5;

m is 2-5;

$R^1$, $R^2$ independently are H or $C_{1-4}$alkyl; or any pharmaceutically acceptable salt or hydrate thereof.

As used herein, "accessible combination thereof" means any combination of the substituents on the phenyl moiety that is available by chemical synthesis and is stable. $C_{1-4}$alkyl means a straight or branched chain alkyl having from 1 to 4 carbons.

Formula (I) compounds are prepared from corresponding phenylalkyl 2-mercaptoimidazoles by processes such as shown in Scheme I, below. The starting phenylalkyl-2-mercaptoimidazoles are prepared from corresponding benzaldehydes or phenylalkylaldehydes by known processes such as shown in Scheme II, below, and described in European Patent Specification 125,033, published Nov. 14, 1984. In Scheme I, m and n are as described in Formula (I), $X^1$ is X as in Formula (I) except OH, and Z is bromo, chloro, fluoro, or iodo.

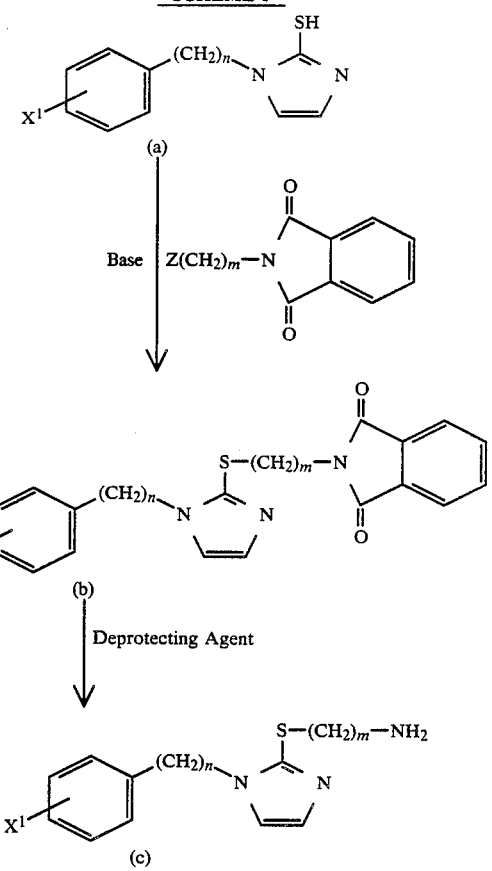

According to Scheme I, when a compound (c), a Formula (I) compound in which $R^1$ and $R^2$ are H, is the desired end product, a compound (a) and a base such as 1,8-diazabicyclo[5.4.0]undec-7-ene (DBU), 1,5-diazabicyclo[4.3.0]non-5-ene (DBN), potassium carbonate, or preferably, potassium hydroxide in a suitable solvent, preferably dimethylformamide and water, are treated with a haloalkyl phthalimide, preferably a bromoalkyl phthalimide, and heated at 50° C. to 100° C., preferably 95° C. to yield compound (b). Thereafter a compound (b) in a suitable organic solvent, preferably ethanol, is treated with a deprotecting agent such as sodium hydroxide, sodium methoxide, potassium hydroxide, or, preferably, hydrazine hydrate, to yield compound (c), as in Example 1, below.

Formula (I) compounds in which $R^1$ and $R^2$ are $C_{1-4}$alkyl are prepared by S-alkylation with a dialkylaminoalkyl halide, preferably chloride, in the presence of a strong base such as potassium hydroxide, using aqueous dimethylformamide or aqueous ethanol as the solvents, as illustrated in Example 6. Formula (I) compounds in which $R^1$ is H and $R^2$ is $C_{1-4}$alkyl are prepared by reacting a compound (c) with an appropriate alkyl aldehyde at pH 6-8 in a suitable solvent, preferably methanol, at 25° C. in the presence of sodium cyanoborohydride as in Example 7, below.

Formula (I) compounds in which X is OH are prepared from a compound (c) in which $X^1$ is $C_{1-4}$alkoxy using known hydrolysis methods, for example by treatment with boron tribromide or hydrogen bromide in an appropriate solvent as exemplified in Example 3.

The phenylalkyl-2-mercaptoimidazoles used as starting materials in Scheme I are prepared from corresponding benzaldehydes or phenylalkylaldehydes using known processes such as shown in Scheme II below. The starting benzaldehydes and phenylalkylaldehydes are known and can be synthesized according to published procedures or can be obtained readily from various commercial suppliers. In Scheme II, $X^1$ is X as in Formula (I) except OH, n' is 1–5, and g is 0–4.

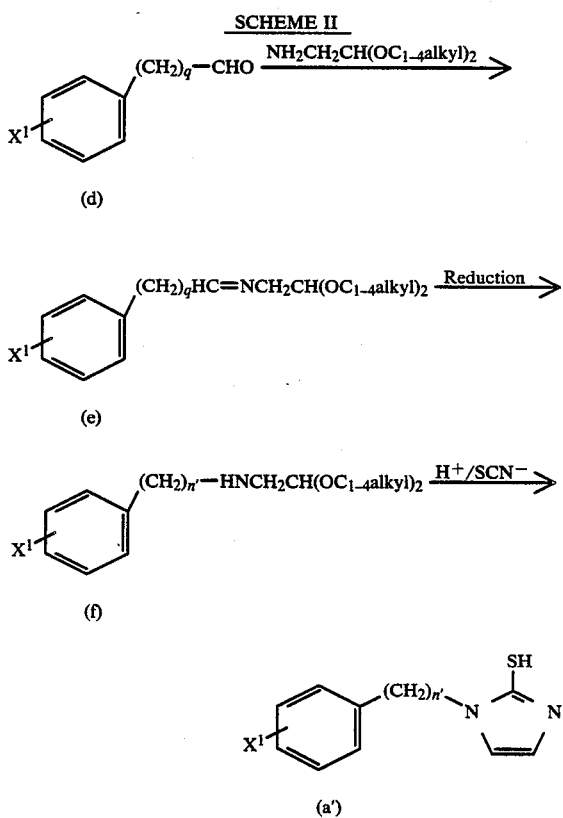

(d)

(e)

(f)

(a')

According to Scheme II, a compound (d) in a suitable organic solvent is reacted with an aminoacetaldehyde $diC_{1-4}alkylacetal$ to yield a compound (e). Thereafter, catalytic hydrogenation of a compound (e) using a suitable catalyst, preferably palladium on carbon, or reduction of a compound (e) using a suitable reducing agent such as sodium borohydride, lithium aluminum hydride, or aluminum hydride yields a compound (f). Reaction of a compound (f) with an acidic solution of a thiocyanate salt, preferably potassium thiocyanate in hydrochloric acid, yields a compound (a') which is a Scheme I compound (a) in which n is 1–5.

Formula (I) compounds in which n is 0 are synthesized from corresponding phenylimidazoles which are prepared by known processes such as reaction of an appropriately substituted phenyl isothiocyanate with an aminoacetaldehyde $diC_{1-4}alkylacetal$ followed by strong acid catalyzed cyclization, as illustrated in Example 5, below.

In preparing the presently invented compounds of Formula (I), novel intermediate compounds of the following Formula (II) were synthesized:

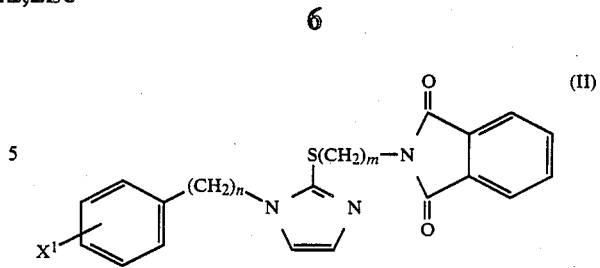

in which:

$X^1$ is H, F, Cl, Br, I, $C_{1-4}$alkyl, CN, $NO_2$, $SO_2NH_2$, COOH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

n is 0–5, and m is 2–5.

Pharmaceutically acceptable acid addition salts of compounds of Formula I are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Because the Formula (I) compounds inhibit DBH activity, they are useful as diuretic, natriuretic, cardiotonic, antihypertensive, and vasodilator agents, as well as antiulcerogenic and anti-Parkinsonian agents.

Listed in Table I are Formula (I) compounds that were tested for in vitro DBH inhibition by a standard procedure for assaying conversion of tyramine to octopamine in the presence of DBH. J. J. Pisano, et al., *Biochim. Biophys. Acta,* 43, 566–568 (1960). Octopamine was assayed following sodium periodate oxidation to p-hydroxybenzaldehyde by measuring spectrophotometric absorbance at 330 nm. Inhibition is given in molar concentration of compound at which DBH activity was halved ($IC_{50}$). Fusaric acid, by this test, has an $IC_{50}$ of $8 \times 10^{-7}M$; 2-(2-aminoethylthio)-1-(3,5-difluorobenzyl)-imidazole has an $IC_{50}$ of $1.8 \times 10^{-3}M$.

Spontaneously hypertensive rats were treated with 2-(2-aminoethylthio)-1-(3,5-difluorobenzyl)imidazole at a dose of 50 mg/kg intraperitoneally, and mean arterial blood pressure was monitored for four hours using an indwelling cannula in the femoral artery. When compared to vehicle treated controls, the animals treated with this compound exhibited significant blood pressure reductions within 30 minutes following treatment and exhibited their lowest blood pressures 3–4 hours after administration. The maximal blood pressure reduction was approximately 10 mmHg.

Formula (I) compounds are incorporated into convenient pharmaceutical dosage forms such as capsules, tablets, or liquids for ingestion, injection, or inhalation. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any material used to give prolonged release of the active compound, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula (I) in a pharmaceutical dosage unit as described above will be an efficacious, nontoxic guantity selected from the range of 0.1–100 mg/kg of active compound, preferably 0.1–50 mg/kg. The selected dose is administered to a human patient in need of DBH inhibition from 1–6 times daily, orally, rectally, by injection, by inhalation, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals, including humans, comprises administering internally to a subject an effective DBH inhibiting amount of a Formula (I) compound.

The method of this invention of reducing blood pressure in mammals, including humans, comprises administering internally to a subject an effective amount of a Formula (I) compound.

The following examples are illustrative of preparation of Formula (I) compounds. The examples are not intended to limit the scope of the invention as defined hereinabove and as claimed below.

EXAMPLE 1

2-(2-Aminoethylthio)-1-(3,5-difluorobenzyl)-imidazole Dihydrochloride 1-(3,5-Difluorobenzyl)-2-mercaptoimidazole (2.26 g, 0.010 mole) and potassium hydroxide (0.56 g, 0.010 mole) were dissolved in dimethylformamide (10 ml) and water (0.5 ml), with stirring under argon at ambient temperature, and N-(2-bromoethyl)phtalimide (2.54 g, 0.010 mole) was added in portions as a solid over one hour. Following addition, the reaction mixture was stirred at ambient temperature for five hours, and then heated at 95° C. for two hours. The reaction mixture was then cooled, diluted with water, and extracted three times with ether. Concentration of the combined ether extracts gave 4.8 g of a yellow oil. This was triturated with several portions of boiling ether. The combined ether solutions were concentrated to give 2.25 g (5.64 mole, 56%) of the 2-mercaptoethylphtahalimide intermediate. This was dissolved in ethanol (10 ml) and hydrazine hydrate (283 mg, 5.64 mmole) was added. The reaction mixture was stirred for 16 hours at ambient temperature and then was refluxed for one hour. The white precipitate (phthalhydrazide) was filtered from the cooled reaction mixture and the filtrate concentrated to a yellow oil (1.54 g). The oil was triturated twice with boiling ether and the combine ether triturates filtered and treated with a slight excess of ethereal hydrogen chloride. The white precipitate was filtered (450 mg) and then recrystallized from ethanol-ether to give 350 mg (18%) of 2-(2-aminoethylthio)-1-(3,5-difluorobenzyl)-imidazole dihydrochloride, mp 201°–202° C.

EXAMPLE 2

2-(2-Aminoethylthio)-1-(4-chlorophenyl)imidazole

The procedure of Example 1 wherein 1-(3,5-difluorobenzyl)-2-mercaptoimidazole is replaced by 1-(4-chlorophenyl)-2-mercaptoimidazole yields 2-(2-aminoethylthio)-1-(4-chlorophenyl)imidazole.

EXAMPLE 3

2-(2-Aminoethylthio)-1-(4-hydroxybenzyl)imidazole

The Example 1 process wherein 1-(3,4-difluorobenzyl)-2-mercaptoimidazole is replaced by 1-(4-methoxybenzyl)-2-mercaptoimidazole yields 2-(2-aminoethylthio)-1-(4-methoxybenzyl)imidazole. Treatment of this compound in methylene chloride with boron tribromide yields 2-(2-aminoethylthio)-1-(4-hydroxybenzyl)imidazole.

EXAMPLE 4

2-(2-Aminoethylthio-1-(phenylethyl)imidazole

The Example 1 process wherein 1-(3,5-difluorobenzyl)-2-mercaptoimidazole is replaced by 1-(phenylethyl)-2-mercaptoimidazole yields 2-(2-aminoethylthio)-1-(phenylethyl)imidazole.

EXAMPLE 5

2-(2-Aminoethylthio)-1-(4-methoxyphenyl)imidazole

A solution of 10 g (0.06 mole) of p-methoxyphenyl isothiocyanate in 100 ml of chloroform was treated with 6.3 g (0.06 mole) of aminoacetaldehyde dimethyl acetal. The solvent was evaporated and the residue was recrystallized from ethanol to yield N-(p-methoxyphenyl)-N'-($\beta,\beta$-dimethoxyethyl)thiourea, 9.2 g (57%). A suspension of this thiourea in a solution of 5 ml of concentrated sulfuric acid and 20 ml of water was refluxed for 3 hours. The mixture was cooled and a solid was filtered, washed with water, and dried. Recrystallization from ethanol gave 1-(4-methoxyphenyl)-2-mercaptoimidazole, 4.9 g (70%), mp 215°–217° C.

The Example 1 procedure wherein 1-(3,5-difluorobenzyl)-2-mercaptoimidazole is replaced by 1-(4-methoxyphenyl)-2-mercaptoimidazole yields 2-(2-aminoethylthio)-1-(4-methoxyphenyl)imidazole.

EXAMPLE 6

2-(2-Dimethylaminoethylthio)-1-(3,5-difluorobenzyl)imidazole Dihydrochloride 1-(3,5-Difluorobenzyl)-2-mercaptoimidazole (2.26 g, 0.010) and potassium hydroxide (0.056 g, 0.010 mole) are dissolved in dimethylformamide (10 ml) containing water (0.5 ml) with stirring under argon at ambient temperature. To this solution is added dropwise 2-dimethylaminoethyl chloride (1.08 g, 0.010 mole) in toluene (10 ml). [This solution is prepared by stirring 1.44 g of dimethylaminoethyl chloride hydrochloride with an excess of sodium hydroxide pellets in the presence of toluene (10 ml) and a few drops of water, followed by filtering the solution of neutralized base.] The reaction mixture is warmed to 95° C., stirred at this temperature for one hour, cooled and then diluted with water. The layers are shaken together and separated and then the aqueous phase is extracted twice with ether. The toluene and ether extracts are combined and the solvents are removed in vacuo. The residual oil is dissolved in ether and hydrogen chloride in ether is added slowly with stirring until a slight excess is present. The precipitated white crystalline solid is filtered and recrystallized from ethanol ether to give 2-(2-dimethylaminoethylthio)-1-(3,5-difluorobenzyl)imidazole dihydrochloride.

EXAMPLE 7

2-(2-Propylaminoethylthio)-1-(3,5-difluorobenzyl)imidazole Dihydrochloride

To a solution of 2-(2-aminoethylthio)-1-(3,5-diflorobenzyl)imidazole (2.69 g, 0.010 mole) in absolute methanol (25 ml) is added 5 N hydrochloric acid methanol (1 ml, 0.005 mole) followed by propionaldehyde (4.25 g, 0.10 mole) and sodium cyanoborohydride (0.38 g, 0.006 mole). The reaction mixture is stirred at 25° C. for 72 hours and then concentrated hydrochloric acid is added until the pH is at least 2. The volatiles are removed in vacuo and then the residue is partitioned between water and ether. The layers are shaken together and separated, the pH of the aqueous extract is adjusted to greater than 10 with solid potassium hydroxide and then the product is extracted into ether. The ether extract is dried with anhydrous magnesium sulfate and then hydrogen chloride in ether is added slowly until a slight excess is present. The precipitated solid is filtered and recrystallized from ethanol-ether to give 2-(2-propylaminoethylthio)-1-(3,5-difluorobenzyl)imidazole dihydrochloride.

EXAMPLE 8

An oral dosage form for administering the presently invented compounds is produced by screening, mixing, and filling into hard gelatin capsules the ingredients in the proportions shown in Table I, below.

TABLE

| Ingredients | Amounts |
|---|---|
| 2-(2-Aminoethylthio)-1-(3,5-difluorobenzyl)imidazole | 50 mg |
| magnesium stearate | 5 mg |
| lactose | 75 mg |

EXAMPLE 9

The sucrose, calcium sulfate dihydrate, and Formula (I) compound shown in Table II below, are mixed and granulated in the proportions shown with a 10% gelatin solution. The wet granules are screened, dried, mixed with the starch, talc and stearic acid, screened, and compressed into a tablet.

TABLE II

| Ingredients | Amounts |
|---|---|
| 2-(2-Aminoethylthio)-1-(3,5-difluorobenzyl)imidazole | 100 mg |
| calcium sulfate dihydrate | 150 mg |
| sucrose | 20 mg |
| starch | 10 mg |
| talc | 5 mg |
| stearic acid | 3 mg |

EXAMPLE 10

2-(2-Aminoethylthio)-1-(3,5-difluorobenzyl)-imidazole dihydrochloride, 75 mg, is dispursed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of the formula:

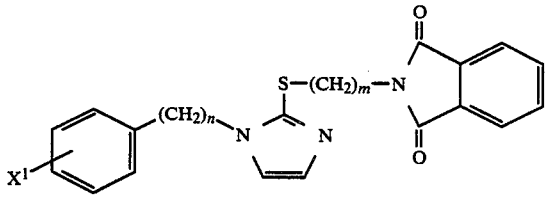

in which:

$X^1$ is H, F, Cl, Br, I, $C_{1-4}$alkyl, CN, $NO_2$, $SO_2NH_2$, COOH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2$-$C_aH_{2a+1}$ wherein a is 1-5, or any accessible combination thereof of up to 5 substituents;

n is 0-5; and m is 2-5.

* * * * *